(12) United States Patent
Shirai

(10) Patent No.: US 7,179,227 B2
(45) Date of Patent: Feb. 20, 2007

(54) SKIN CONDITION OBSERVATION APPARATUS

(75) Inventor: Yasuo Shirai, Chiba (JP)

(73) Assignee: Moritex Corporation, Tokyo (JP)

( * ) Notice: Subject to any disclaimer, the term of this patent is extended or adjusted under 35 U.S.C. 154(b) by 520 days.

(21) Appl. No.: 10/642,683

(22) Filed: Aug. 19, 2003

(65) Prior Publication Data

US 2004/0086456 A1    May 6, 2004

(30) Foreign Application Priority Data

Aug. 20, 2002   (JP)   ............................. 2002-239281

(51) Int. Cl.
*A61B 5/00*   (2006.01)
(52) U.S. Cl. ..................................... 600/306
(58) Field of Classification Search ........ 600/309–310, 600/407
See application file for complete search history.

(56) References Cited

U.S. PATENT DOCUMENTS 4,265,539 A * 5/1981 Gaffard ...................... 356/520
6,794,633 B2 * 9/2004 Iwasaki ....................... 250/221

OTHER PUBLICATIONS

English Language Abstract of JP 2002-85356.

* cited by examiner

*Primary Examiner*—Charles A. Marmor, II
*Assistant Examiner*—Vikram Sundararaman
(74) *Attorney, Agent, or Firm*—Greenblum & Bernstein, P.L.C.

(57) ABSTRACT

A skin condition observation apparatus having a sebum amount measuring device adapted for bringing a sebum sampling surface into contact with skins and optically measuring the amount of deposited sebum, wherein the sebum amount measuring device comprises an orthogonal prism having two reflection surfaces orthogonal with each other in which one reflection surface is exposed as the sebum sampling surface, and a light emitting element for illuminating a light to one of the reflection surfaces and a photoreceiving element for detecting the intensity of a reflection light reflected on the two reflection surfaces and returned therefrom are located being opposed to the hypotenuse surface at the back of the orthogonal prism, with their optical axes being in parallel with each other, whereby the sebum amount measuring device of the skin condition observation apparatus can be manufactured with no requirement for glass fabrication at high accuracy, troublesome and delicate alignment for optical axes with respect to the angle, at a low cost and in a reduced-size.

5 Claims, 2 Drawing Sheets

SKIN CONDITION OBSERVATION APPARATUS

BACKGROUND OF THE INVENTION

1. Field of the Invention

The present invention concerns a skin condition observation apparatus having a sebum amount measuring device for optically measuring the amount of deposited sebum by being in contact with skins.

2. Statement of Related Art

A sebum amount measuring device is used for recognizing the conditions of a customer's skins objectively, for example, in a so-called cosmetic salon (cosmetic shop). Since shop attendants can advice cosmetics optimal to the skin conditions based on the result of the observation and the customer is provided with objective data for purchasing such cosmetics, the device is extremely effective for the sales promotion.

Existent sebum amount measuring devices were used by attaching a disposable sebum sampling part made of plastics to the top end of a probe, putting the same on skins to deposit sebum and then measuring the intensity of a reflection light or a transmission light from the sebum deposited on the part and measuring the amount of sebum based on the result of the measurement.

In a case of using a disposable sebum sampling part, since the sebum can always be deposited on a new sebum sampling part, maintenance after use is not required and the sebum can be measured accurately with no maintenance on every measurement in a busy shop situation.

As described above, while the disposable part is convenient, since it has to be replaced with new sebum sampling part on every measurement and used part has to be discarded, running cost is increased to result in an economical disadvantage and it increases the volume of wastes. In addition, since the measurement is impossible if the part run out, parts have to be stocked always by a predetermined amount.

In view of the above, it has been proposed a device not requiring consumable parts at all although requiring some maintenance operation such as wiping off the sebum deposited on the sebum sampling surface (refer to Japanese Patent Laid-Open No. 2002-85356).

FIG. 4 shows the measuring method of such a sebum amount measuring device 51, in which the surface of a glass block 52 is formed as a sebum sampling surface 53, and a light incident surface 55 for incidence of a light illuminated from a light emitting element 54 to the sebum sampling surface 53 and a light emitting surface 57 for emission of a light reflected on the sebum sampling surface 53 to a photoreceiving element 56 are formed at the back of the block.

The incident angle of the light to the sebum sampling surface 53 is selected such that it is larger than a critical angle relative to water and smaller than a critical angle relative to sebum. For example, the light emitting element 54 is disposed on an incident optical axis 58 at an incident angle of 50°, and the surface is chamfered such that the light incident surface 55 is in perpendicular to the incident light axis 58. Further, the photoreceiving element 56 is disposed on a reflection light axis 59 at a reflection angle of 50°, and the light emitting surface 57 is chamfered such that it is in perpendicular to the reflection light axis 59.

According to the constitution described above, since the incident angle of the light is selected such that it is larger than the critical angle relative to water and smaller than the critical angle relative to sebum, even when sebum and water are deposited simultaneously on the sebum sampling surface 53, only the total reflection light from the sebum component reaches the photoreceiving device, while the light illuminated to the water component is transmitted with no reflection, so that the amount of the sebum can be measured accurately.

Further, since sebum and water can be removed simply from the sebum sampling surface 53 formed to the glass block 52 by merely wiping off with an alcohol or the like, disposable consumable parts such as the existent sebum sampling part are no more necessary.

However, since the incident light axis 58 and the reflection light axis 59 formed at an angle of 100° are not actually visible, it is extremely difficult to accurately position such that the optical axes 58 and 59 and the optical axes for the light emitting element 54 and the photoreceiving element 56 are aligned, as well as it is also difficult to form the light incident surface 55/light emitting surface 57 at the angle in accordance with the incident angle/reflection angle on the back of the glass block 52. Since fabrication accuracy is required in any of the cases, this results in a problem of increasing the manufacturing cost.

Further, since the light emitting element 54 and the photoreceiving element 56 are disposed on both right and left sides of the glass block 52 while sandwiching the block, the size of the sensor portion is enlarged to result in a problem that it can not be installed at a narrow.

In view of the above, it is a technical subject of the present invention, at first, to save requirement for glass fabrication at high accuracy or troublesome alignment between optical axes, and to enable size reduction for the sensor portion of a sebum amount measuring device and, secondly, provide a small sized skin condition observation apparatus incorporated with a sebum amount measuring device.

SUMMARY OF THE INVENTION

For solving the subject, the present invention provides, in accordance with a first feature, a skin condition observation apparatus having a sebum amount measuring device adapted for bringing a sebum sampling surface into contact with skins and optically measuring the amount of deposited sebum, wherein the sebum amount measuring device comprises an orthogonal prism having two reflection surfaces orthogonal with each other in which one reflection surface is exposed as the sebum sampling surface, and a light emitting element for illuminating a light to one of the reflection surfaces and a photoreceiving element for detecting the intensity of a reflection light reflected on the two reflection surfaces and returned therefrom are located being opposed to the hypotenuse surface at the back of the orthogonal prism, with their optical axes being in parallel with each other.

According to the invention, since one of the reflection surfaces of the orthogonal prism is used as the sebum sampling surface, the light irradiated from the light emitting element to one reflection surface is reflected on the two reflection surfaces, and the reflection light always returns along the parallel optical channel relative to the illumination light, irrespective of the illumination angle of the illumination light.

Accordingly, so long as the optical axes for the light emitting element and the photoreceiving element are made in parallel with each other, there is no requirement for aligning the angles of the respective optical axes and measurement is possible in a case, for example, designed to the incident light axis at 40°, with no accurate alignment to 40°.

Further, since the light emitting element and the photoreceiving element can be located in parallel so as to oppose the hypotenuse surface of the orthogonal prism, the size of the sensor portion can be reduced.

However, since the distance between the parallel optical channels of the illumination light and the reflection light varies depending on the positions of the light emitting element and the photoreceiving element relative to the orthogonal prism, it is necessary that the distance between the parallel optical channels and the distance between the light emitting element and the photoreceiving element have to be aligned. This may be attained, for example, by merely attaching the light emitting element and the photoreceiving element on one identical substrate with a distance being constant and by displacing the light emitting element and the photoreceiving element in this state along the lateral direction of the parallel optical channels integrally as in a preferred embodiment of the invention so as to maximize the intensity of the light detected by the photoreceiving element.

Further, according to the experiment made by the inventor, it has been found that since the content of water deposited on the sebum sampling surface upon contact with skins is little and it soon evaporates, no particular measuring error is caused due to the effect of water.

Accordingly, it is not necessary for illumination at an angle of illumination larger than the critical angle relative to water and smaller than the critical angle relative to sebum.

Further, in another embodiment where an infrared light is illuminated and the intensity of the infrared reflection light is measured, even when a visible light enters from the outside transmitting through the sebum sampling surface exposed to the outside, this does cause error to the result of detection under the effect thereof.

Further, the invention provides, in accordance with a second feature, a skin condition observation apparatus having an imaging device for photographing enlarged images of skins and a sebum amount measuring device adapted for bringing a sebum sampling surface into contact with skins and optically measuring the amount of deposited sebum located to a measuring head formed with a skin contact surface, wherein the imaging device comprises an illumination device for illuminating an illumination light to skins through an observation aperture formed in the skin contact surface of the measuring head and an imaging element for photographing the images of skins taken from the observation apertures,.

the sebum amount measuring device comprises an orthogonal prism having two reflection surfaces orthogonal with each other in which one reflection surface is exposed as the sebum sampling surface, and a light emitting element for illuminating a light to one of the reflection surfaces and a photoreceiving element for detecting the intensity of a reflection light reflected on the two reflection surfaces and returned therefrom are located being opposed to the hypotenuse surface at the back of the orthogonal prism, with their optical axes being in parallel with each other in the measuring head, and a digital display for display of images photographed by the imaging device and the result of the measurement of the sebum amount measuring device is provided.

According to the second feature of the invention, since the sebum amount measuring device can be located with the reduced size on the front of the measuring head incorporating the imaging element, enlarged images of the skins can be picked-up and the sebum amount can be measured by bringing the measuring head into contact with skins.

Further, since the display panel is disposed integrally, enlarged images can be projected only by the device and the result of measurement for the amount of sebum can be displayed.

Further, in a case where a moisture sensor is provided as a modified embodiment, not only the amount of sebum but also the data for the moisture content can also be obtained.

BRIEF DESCRIPTION OF THE DRAWINGS

Preferred embodiments of this invention will be described in details based on the drawings, wherein.

DESCRIPTION OF PREFERRED EMBODIMENTS OF THE INVENTION

Figure 1:
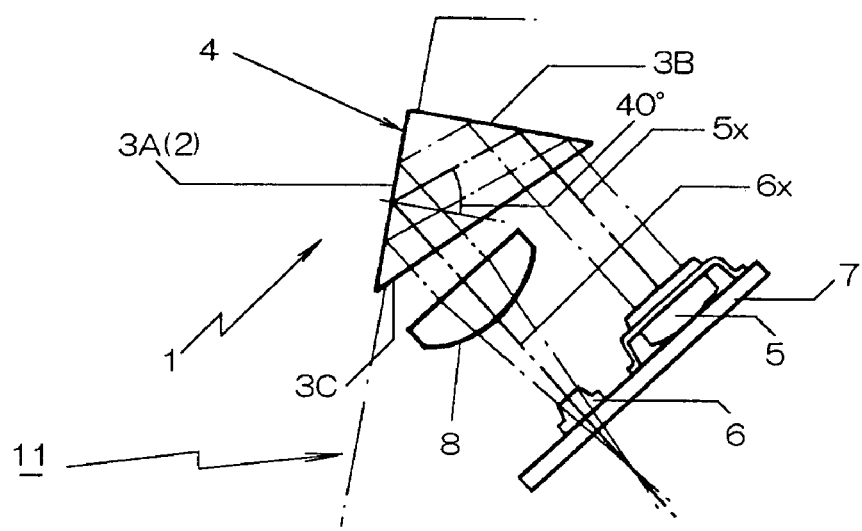
FIG. 1 is an explanatory view showing a main portion of a skin condition observation apparatus according to the invention.

Preferred embodiments of the present invention are to be described specifically with reference to the drawings.

A sebum amount measuring device 1 incorporated in a skin condition observation apparatus is adapted for bringing a sebum sampling surface 2 into contact with skins and optically measuring the amount of deposited sebum.

The sebum sampling surface 2 is formed such that a reflection surface 3A of an orthogonal prism 4 having two reflection surfaces 3A, 3B orthogonal with each other is exposed so as to be in contact with skins.

Then, at the back of the orthogonal prism 4, a light emitting diode (light emitting element) 5 for illuminating an infrared light at 880 nm to one reflection surface 3B and a photodiode (photoreceiving element) 6 for detecting the intensity of a reflected infrared light reflected on the two reflection surfaces 3B, 3A and returned therefrom are disposed opposed to the hypotenuse surface 3C and mounted on an identical substrate 7 with the respective optical axes 5×, 6× in parallel with each other, and a lens 8 for collecting the reflection light is located on the optical axis 6× of the photodiode 6.

In this case, since the light illuminated from the light emitting diode 5 is reflected on the two reflection surfaces 3B, 3A orthogonal with each other of the orthogonal prism 4 and, accordingly, the optical channel of the illumination light and the optical channel of the reflection light are always in parallel with each other irrespective of the angle of incidence to the sebum sampling surface 2, no high accuracy is required for the mounting angle to the substrate 7.

Further, since the light emitting diode 5 and the photodiode 6 are disposed opposed to the hypotenuse surface 3C at the back of the orthogonal prism 4 with the respective optical axes 5×, 6× being in parallel with each other, the entire constitution can be made compact.

When an optional point on the sebum sampling surface 2 is defined as an observation center P, and the incident angle is set to 40°, the substrate 7 and the attaching position thereof can be designed by drawing incident optical channel/reflection optical channel that are entered/reflected at incident angle/reflection angle of 40° to the observation center P and aligning the optical axis 5× of the light emitting diode (light emitting element) 5 and the optical axis 6x of the photodiode (photoreceiving element) 6.

In a case where the mounting position or the mounting angle of the substrate 7 is deviated from the design, since the distance between the optical channels is also changed, the position may be controlled in actual assembling such that the intensity of light detected by the photodiode 6 is maximized by reflecting the light illuminated from the light emitting diode 5 at the orthogonal prism 4. Since there is no requirement for considering the mounting angle, control operation can be conducted easily.

The constitution of the skin condition observation apparatus 11 having a sebum amount measuring device 1 according to the present invention is as has been described above and the operation thereof is to be described.

At first, the sebum sampling surface 2 is removed with contamination by wiping, for example, with an alcohol and is brought into contact with skins of a person whose sebum amount is to be measured and sebum is deposited thereon.

Then, when the light emitting diode is lit, an infrared light proceeds along the optical axis 5x, enters from the hypotenuse surface 3C to the orthogonal prism 4 and then reflected on the reflection surface 3B to reach the reflection surface 3A, on which it is reflected again and emitted through the hypotenuse surface 3C from the orthogonal prism 4. Then, the reflection light proceeds along the optical axis 6x and reaches the photodiode 6.

In this case, since the reflection surfaces 3A and 3B are orthogonal with each other, the illumination light and the reflection light are maintained in parallel with each other within the orthogonal prism 4. Further, since the light passes through the hypotenuse surface 3C twice upon incidence/emission to and from the orthogonal prism 4, even when the light is refracted upon every passage through the slope 3C, the refraction is offset upon incidence and emission and the illumination light and the reflection light are kept in parallel with each other.

Further, since the reflection surface 3B is not exposed, the reflectance is always constant. While on the other hand, since the reflection surface 3A constitutes a sebum sampling surface 2, sebum is deposited and the reflectance changes depending on the amount of deposition. That is, the reflectance lowers and the intensity of light detected by the photodiode 6 lowers as the deposition amount increases.

Accordingly, the amount of sebum can be detected based on the intensity of light by previously determining a relation experimentally between the deposition amount of sebum and the intensity of light.

In this case, since the light emitting diode 5 illuminates the infrared light and the intensity of the reflection light of the infrared light is detected by the photodiode 6, even when a visible light enters transmitting the sebum sampling surface 2 exposed to the outside, error is not caused to the result of detection under the effect thereof.

Figure 2:
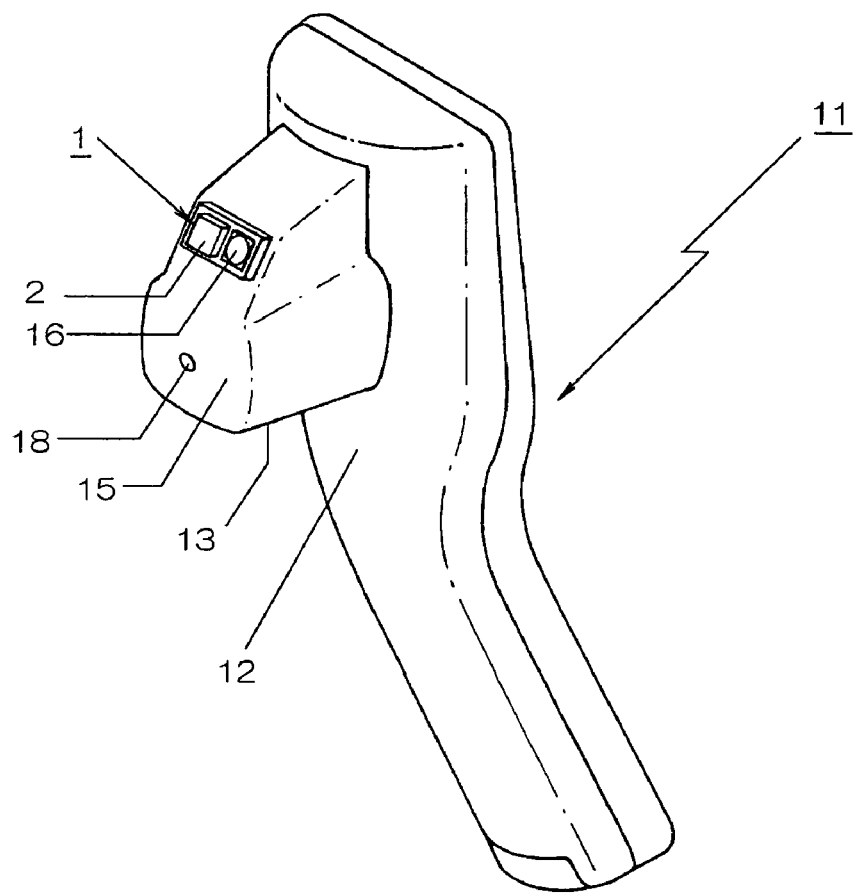
FIG. 2 is an outer view showing a skin condition observation apparatus according to the invention.
Figure 3:
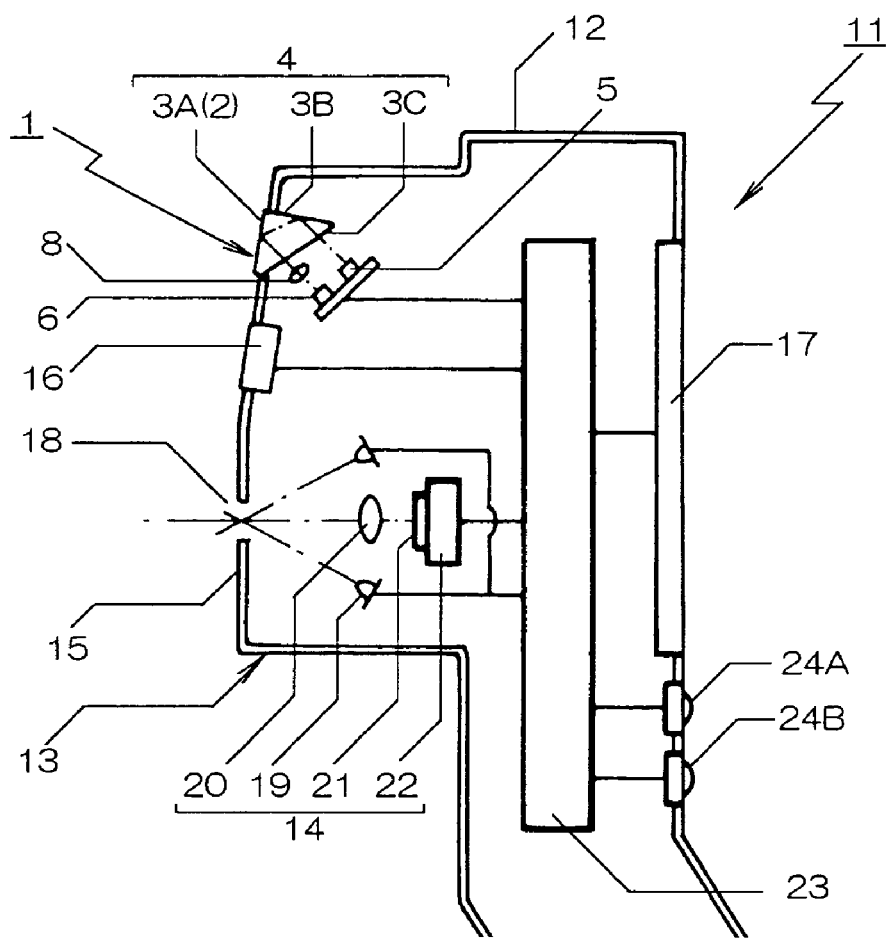
FIG. 3 is a block diagram thereof.
Figure 4:
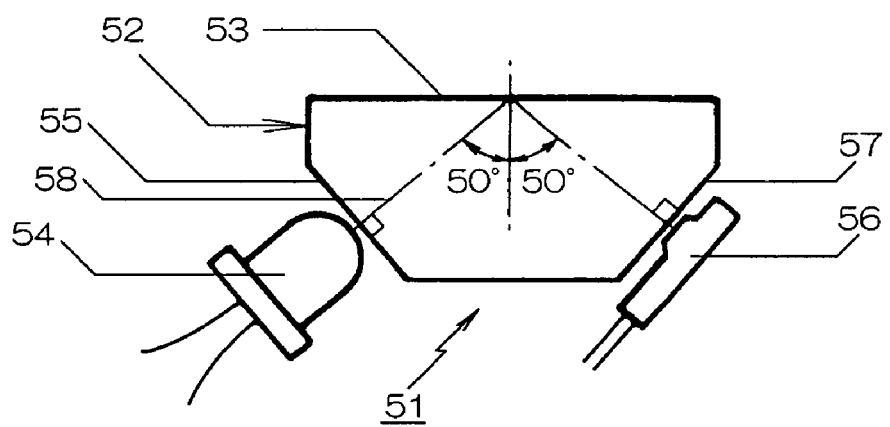
FIG. 4 is a explanatory view showing an existent sebum amount measuring device.

FIG. 2 is an explanatory view showing a skin condition observation apparatus incorporating the sebum amount measuring device described above and FIG. 3 is a block diagram thereof. Components in common with those in FIG. 1 carry same reference numerals for which detailed explanations are to be omitted.

In the skin condition observation apparatus 11, a measuring head 13 is protruded at the front of a casing 12, an imaging device 14 for picking-up enlarged images of skins is disposed inside the head, and a sebum amount measuring device 1 for optically measuring the amount of sebum and a moisture sensor 16 for measuring the moisture content of skins are disposed to a skin contact surface 15 at the top end of the head. A liquid crystal display 17 for display of images picked-up by an imaging device 14 and the result of measurement by the sebum amount measuring device 1 and the moisture sensor 16 is disposed integrally at the back of the casing 12.

The imaging device 14 comprises an illumination device 19 such as a light emitting diode for illuminating an illumination light to skins through an observation aperture 18 formed in the skin contact surface 15 of the measuring head 13, a lens 20 for magnifying images of the skins taken from the observation aperture 18, an imaging element 21 for photographing images focused by the lens 20 and a control unit 22 for outputting the photographed images.

The sebum amount measuring device 1 comprises an orthogonal prism 4 having two reflection surfaces 3A and 3B orthogonal to each other, and one reflection surface 3A is located being exposed as a sebum sampling surface 2 to the skin contact surface 15 of the measuring head 13. A light emitting diode 5 for illuminating a light to one reflection surface 3B and a photodiode 6 for detecting the intensity of a reflection light reflected at the two reflection surfaces 3B, 3A and returned therefrom are located in the measuring head 13 being opposed to the hypotenuse surface 3C on the back of the orthogonal prism 4, with their optical axes 5x, 6x being parallel with each other.

For the moisture sensor 16, a resistance-change type moisture sensor or the like is used and a moisture sensitive sheet thereof is exposed to the skin contact surface 15 of the measuring head 13.

Then, the sebum amount measuring device 1, the moisture sensor 16, the imaging device 14 and the liquid crystal display 17 are connected with a calculative device 23 and, a main switch 24A for turning the imaging device 14, the sebum amount measuring device 1 and the moisture sensor 16 to ON and OFF, and a mode changing switch 24B for changing the images between a static image mode and a dynamic image mode in the ON-state of the imaging device 14 are provided.

The main switch 24A is designed such that the sebum amount measuring device 1 and the moisture sensor 16 are turned ON by pushing once, the sebum amount measuring device 1 and the moisture sensor 16 are turned OFF while the imaging device 14 is turned ON by pushing twice and all the devices are turned OFF by pushing for three times.

According to the constitution described above, when contaminations on the sebum sampling surface 2 of the sebum amount measuring device 1 are wiped off with an alcohol or the like, the skin contact surface 15 of the measuring head 13 is put against skins and the sebum amount measuring device 1 and the moisture sensor 16 are turned ON by the main switch 24A, the amount of sebum deposited on the sebum sampling surface is measured by the sebum amount measuring device 1, and the moisture of skins is measured by the moisture sensor 16, and the result of measurement is displayed on the light crystal display 17.

Accordingly, conditions of skins with respect to the extent for the amount of sebum and the amount of moisture can be explained to a customer while monitoring the display on the liquid crystal display 17 in situ, with no further connection to a computer or the like.

Then, in a state of turning the imaging device 14 to ON by the main switch 24A, when the dynamic image mode is set by the mode changing switch 24B and the skin contact surface 15 of the measuring head 13 is put against the skins, images of the skins inputted through the observation aperture 18 are displayed on the liquid crystal display 17.

Then, in a case where spot or somberness is imaged, for example, when the images are switched to the stationary mode by the mode changing switch 24B, the images are stored and the conditions of the skins can be explained to the customer while monitor the images on the liquid crystal display 7 in situ with no further connection to a computer or the like.

As described above, since the skin condition observation apparatus 11 comprises the sebum amount measuring device 1, the imaging device 14 and the liquid crystal display 17 for display of the measuring result and the images as an all-in-one structure, the skin conditions can be explained to a customer while monitoring the display on the liquid crystal display 17 by the provision of a set of the observation apparatus 11, with no further connection to the computer or the like.

Accordingly, the apparatus can be located even in a shop having only a narrow counter with no room for placing a computer.

Further, since the sebum amount measuring device 1 has a constitution in which one reflection surface 3A of the orthogonal prism 4 is used as the sebum sampling surface 2, and the light emitting diode 5 and the photodiode 6 are located being opposed to the hypotenuse surface 3C thereof, it can be formed in a reduced size and, when it is assembled into the measuring head 13 and formed as the all-in-one type structure, it does not enlarge the size of the observation apparatus 11.

As has been described above, according to the sebum amount measuring device of the invention, since the light emitting element and the photoreceiving element are located being opposed to the hypotenuse surface of the orthogonal prism, with their optical axes being in parallel with each other, the invention can provide excellent effect of not requiring glass fabrication at high accuracy or troublesome alignment between the optical axes and, in addition, capable of reducing the size of the sensor portion.

Further, according to the skin condition observation apparatus of the invention comprising the sebum amount measuring device, the imaging device and the liquid crystal display for the display of the result of measurement and images are arranged as the all-in-one structure, it can provide excellent effects capable of explaining the skin conditions to a customer while monitoring the display and capable of locating even in a shop only having a narrow counter with no room for placing a computer with no worry about the place for location.

The present disclosure relates to subject matter contained in priority Japanese Patent Application No.2002-239,281 filed on Aug. 20, 2002, the contents of which is herein expressly incorporated by reference in its entirety.

What is claimed is:

1. A skin condition observation apparatus having a sebum amount measuring device adapted for bringing a sebum sampling surface into contact with skins and optically measuring the amount of deposited sebum, wherein the sebum amount measuring device comprises an orthogonal prism having two reflection surfaces orthogonal with each other in which one reflection surface is exposed as the sebum sampling surface, and a light emitting element for illuminating a light to one of the reflection surfaces and a photoreceiving element for detecting the intensity of a reflection light reflected on the two reflection surfaces and returned therefrom are located being opposed to the hypotenuse surface at the back of the orthogonal prism, with their optical axes being in parallel with each other, and a processor to calculate the amount of sebum on the skin surface from the intensity of the reflection light received by the photoreceiving element.

2. A skin condition observation apparatus according to claim 1, wherein the light emitting device and the photoreceiving device are mounted on one identical substrate.

3. A skin condition observation apparatus according to claim 1, wherein the illumination light of the light emitting device is an infrared light.

4. A skin condition observation apparatus having a skin contact surface and comprising an imaging device for photographing enlarged images of skins and a sebum amount measuring device adapted for bringing the sebum sampling surface into contact with skins and optically measuring the amount of deposited sebum, wherein the imaging device comprises an illumination device for illuminating an illumination light to skins through an observation aperture formed in the skin contact surface of the measuring head and an imaging element for photographing the images of skins taken from the observation apertures, the sebum amount measuring device comprises an orthogonal prism having two reflection surfaces orthogonal with each other in which one reflection surface is exposed as a sebum sampling surface to the skin contact surface, and a light emitting element for illuminating a light to one of the reflection surfaces and a photoreceiving element for detecting the intensity of a reflection light reflected on the two reflection surfaces and returned therefrom are located in the measuring head being opposed to the hypotenuse surface at the back of the orthogonal prism, with the optical axes thereof being in parallel with each other, and wherein the apparatus further comprises a digital display for display of images photographed by the imaging device and the result of the measurement of the sebum amount measuring device, and wherein a moisture sensor to measure the moisture content of skins is disposed to the measuring head on the side of the skin contact surface.

5. A skin condition observation apparatus according to claim 2, wherein the illumination light of the light emitting device is an infrared light.

* * * * *